United States Patent
Studer

(10) Patent No.: US 6,660,890 B1
(45) Date of Patent: Dec. 9, 2003

(54) PRODUCTION OF OPTICALLY ACTIVE α-HYDROXYACETALS

(75) Inventor: Martin Studer, Basel (CH)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 10/018,365

(22) PCT Filed: Nov. 4, 1999

(86) PCT No.: PCT/EP99/08446

§ 371 (c)(1),
(2), (4) Date: Dec. 19, 2001

(87) PCT Pub. No.: WO01/00545

PCT Pub. Date: Jan. 4, 2001

(30) Foreign Application Priority Data

Jun. 23, 1999 (CH) .............................. 1170/99

(51) Int. Cl.[7] .................. C07C 43/30; C07C 41/00; C07C 27/00
(52) U.S. Cl. ................ 568/599; 568/600; 568/678; 568/691; 568/814; 568/830; 568/862; 568/866
(58) Field of Search ................ 568/599, 600, 568/678, 691, 814, 830, 862, 866

(56) References Cited

U.S. PATENT DOCUMENTS 4,329,487 A * 5/1982 Orita et al.

OTHER PUBLICATIONS

Cho, B.T., et al. "Asymmetric reduction of alpha–keto acetals with potassium 9–0–(1,2–isopropylidene–5–deoxy–D–xylofuranosyl)–9–boratabicyclo'3.3.1 !nonane. Enantioselective synthesis of alpha–hydroxy acetals with high optical purities", Tetrahedron: Asymmetry., vol. 5, No. 7, 1994, pp. 1147–1150.

Takahashi, H. "Highly effective catalytic asymmetric hydrogenations of alpha–keto esters and an alpha–keto acetal with new neutral chiral pyrroliddinebisphosphine–rhodium complexes", Chemistry Letters, No. 5, May 1987, pp. 855–858.

Blaser, H.U., et al., "Enantioselective hydrogenation of alpha–ketoesters with cinchona–modified platinum catalysts: effect of acidic and basic solvents and additives", Journal of Molecular Catalysts, vol. 68, 1991, pp. 215–222.

Studer, M. "Hydrogenation of butane–2,3–dione with heterogeneous cinchona modified platinum catalysts: a combination of an enantioselective reaction and kinetic resolution", Journal of the Chemical Society, Chemical Communications, No. 9, May 1998, pp. 1053–1054.

Studer, M. "Enantioselective hydrogenation of alpha–keto acetals with cinchona modified Pt catalyst", Journal of the Chemical Society, Chemical Communications, No. 17, Sep. 1999, pp. 1727–1728.

* cited by examiner

Primary Examiner—Johann Richter
Assistant Examiner—Sikarl A. Witherspoon
(74) Attorney, Agent, or Firm—Wenderoth, Lind & Ponack, L.L.P.

(57) ABSTRACT

A process for the heterogeneous and enantioselective hydrogenation of prochiral organic α-keto compounds with platinum as the catalyst in the presence of a soluble or immobilized chiral aromatic nitrogen base with at least one basic nitrogen atom adjacent to stereogenic carbon atoms, whereby prochiral α-ketoacetals are hydrogenated to optically active α-hydroxyacetals.

11 Claims, No Drawings

PRODUCTION OF OPTICALLY ACTIVE α-HYDROXYACETALS

This application is a 371 application of PCT/EP99/08446 filed Nov. 4, 1999.

The invention relates to a process for the production of optically active α-hydroxyacetals by means of heterogeneous and enantioselective hydrogenation of prochiral α-ketoacetals with platinum as the catalyst and in the presence of a chiral aromatic nitrogen base with at least one basic nitrogen atom adjacent to stereogenic carbon atoms, for example cinchona alkaloids and derivatives thereof.

Optically active α-hydroxyacetals are valuable intermediates in the production of natural compounds [B. T. Cho et al. in Tetrahedron: Asymmetry Vol. 5, No. 7 (1994), pages 1147 to 1150], pharmaceutical active ingredients and pesticides. Cho et al. also describe the asymmetric reduction of α-ketoacetals in homogeneous phase with stoichiometric quantities of a special asymmetric borohydride, namely potassium-9-O-(1,2-isopropylidene-5-deoxy-α-D-xylofuranosyl)-9-boratabicyclo[3.3.1]nonane. H. Takahashi et al. describes in Chemistry Letters (1987), pages 855 to 858 the asymmetric hydrogenation of α-ketopropionic acid methyl ester and 1,1-dimethoxypropan-2-one with chiral rhodium/diphosphine complexes, whereby the optical yields of 1,1dimethoxypropan-2-ol are significantly lower than those of α-hydroxypropionic acid methyl ester. Furthermore, enzymatic reduction processes are known, see for example J. Peters et al. in Tetrahedron: Asymmetry Vol.4, No. 7 (1993), pages 1683 to 1692, and C.-H. Wong et al., J. Am. Chem. Soc. 1985, 107, pages 4028 to 4031. For economic reasons, the above-described processes are not suitable for processes on an industrial scale, primarily because of the high costs in the production of catalysts, which, in addition, can only be separated from the homogeneous reaction mixtures with difficulty and also cannot be reused. In enzymatic or microbial processes, often only low concentrations of substrate may be used, and the necessary reaction control requires complicated reaction equipment.

As long ago as 1979, Orito et al. described that optically active α-hydroxycarboxylates were obtainable in good optical yields by means of hydrogenation of α-ketocarboxylates with platinum metal catalysts in the presence of a cinchona alkaloid. The influence of solvents and other reaction conditions in this hydrogenation Is described by H. U. Blaser et al. in J. of Mol. Cat. 68 (1991), pages 215 to 222. Further studies have shown [see H. U. Blaser et al. in Catalysis Today 37 (1997), pages 441 to 461] that the catalytic hydrogenation system has high substrate specificity. Even the use of α-diketones instead of the α-keto-carboxylates (optical yield, ee up to 95%) leads to considerably lower optical yields (ee only 39 to 50%, see also W. A. H. Vermeer et al. in J. Chem. Soc., Chem. Comm., 1993, pages 1053 to 1054 and M. Studer et al. in J. Chem. Soc., Chem. Comm., 1998, pages 1053). The effect is even more marked when using α-ketomethylethers, and an optical yield of only about 12% ee is obtained (H. U. Blaser et al. in Heterogeneous Catalysis and Fine Chemicals, Elsevier Science Publishers B. V., Amsterdam, 1998, pages 153 to 163).

It has now surprisingly been found that the carbonyl group in α-ketoacetals can be enantio-selectively catalytically hydrogenated with high selectivity and a high yield, with a simultaneously high optical yield (ee to over 95%) even with high concentrations of substrate and even without solvents, if the reaction is carried out in the presence of platinum as the catalyst and in the presence of a soluble or immobilised cinchona alkaloid or derivatives thereof. The catalyst activity is excellent and the catalyst can be simply separated by filtration processes and optionally reused after purification and reactivation. The process is therefore suitable for usage on an industrial scale. This hydrogenation possibility is even more surprising, as α-ketoketals cannot be hydrogenated by this process.

The object of the invention is thus a process for the heterogeneous and enantioselective hydrogenation of prochiral organic α-keto compounds with platinum as the catalyst in the presence of a soluble or immobilised chiral aromatic nitrogen base with at least one basic nitrogen atom adjacent to the stereogenic carbon atoms, which is characterised in that prochiral α-ketoacetals are hydrogenated to optically active α-hydroxyacetals.

Being adjacent to stereogenic carbon atoms may mean, for example, that the basic nitrogen atom is in β- and more preferably in α-position to at least one stereogenic carbon atom.

The prochiral α-ketoacetals in question may be saturated or unsaturated, open-chained or cyclic compounds, which contain preferably 5 to 30, most preferably 5 to 20 carbon atoms, which are unsubstituted or substituted by radicals that are stable under the hydrogenation conditions. The carbon chain may be interrupted by hetero atoms preferably from the group —O—, =N— and —NR'—, wherein R' is H, $C_1$–$C_8$-alkyl, preferably $C_1$–$C_4$-alkyl, $C_5$- or $C_6$-cycloalkyl, $C_6$–$C_{10}$-aryl, for example phenyl or naphthyl, phenyl or phenylethyl.

The α-ketoacetals preferably correspond to formula I

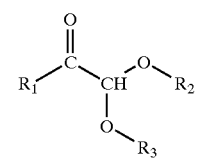

wherein $R_1$, $R_2$ and $R_3$, independently of one another, signify a monovalent, saturated or unsaturated, aliphatic radical with 1 to 12 carbon atoms, a saturated or unsaturated cyclo-aliphatic radical with 3 to 8 carbon atoms, a saturated or unsaturated heterocycloaliphatic radical with 3 to 8 ring members and one or two hetero atoms from the group O, N and NR', a saturated or unsaturated cycloaliphatic-aliphatic radical with 4 to 12 carbon atoms, a saturated or unsaturated heterocycloaliphatic-aliphatic radical with 3 to 12 carbon atoms and one or two hetero atoms from the group O, N and NR', an aromatic radical with 6 to 10 carbon atoms, a heteroaromatic radical with 4 to 9 carbon atoms and one or two hetero atoms from the group O and N, an aromatic-aliphatic radical with 7 to 12 carbon atoms or a heteroaromatic-aliphatic radical with 5 to 11 carbon atoms and one or two hetero atoms from the group O and N, whereby R' is H, $C_1$–$C_8$-alkyl, preferably $C_1$–$C_4$-alkyl, $C_5$- or $C_6$-cyclo-alkyl, $C_6$–$C_{10}$-aryl, for example phenyl or naphthyl, phenyl or phenylethyl, $R_1$ and $R_2$ together are $C_1$–$C_6$-alkylene or $C_3$–$C_8$-1,2-cycloalkylene; or $C_2$–$C_4$-alkylene or $C_3$–$C_8$-cycloalkylene which are condensed with 1,2-phenylene, and $R_3$ has the above-mentioned significances, $R_2$ and $R_3$ together signify $C_1$–$C_6$-alkylene, $C_1$–$C_8$-alkylidene, $C_3$–$C_8$-1,2-cycloalkylene, $C_3$–$C_8$-cycloalkylidene, benzylidene, 1,2-phenylene, 1,2-pyridynylene, 1,2-naphthylene; or $C_3$–$C_4$-alkylene or $C_3$–$C_8$-1,2-cycloalkylene which are condensed with 1,2-cycloalkylene or with 1,2-phenylene, and $R_1$ has the above-mentioned significances, and $R_1$, $R_2$ and $R_3$ are unsubstituted or substituted by one or more identical or different radicals selected from the group $C_1$–$C_4$-alkyl, $C_2$–$C_4$-alkenyl, $C_1$–$C_4$-alkoxy, $C_1$–$C_4$-halogen-alkyl, $C_1$–$C_4$-hydroxyalkyl, $C_1$–$C_4$-alkoxymethyl or -ethyl, $C_1$–$C_4$-halogenalkoxy, cyclohexyl, cyclohexyloxy, cyclohexylmethyl, cyclohexylmethyloxy, phenyl, phenyloxy, benzyl, benzyloxy, phenylethyl, phenylethyloxy, halogen, —OH, —$OR_4$, —OC(O)—$R_4$, —$NH_2$, —$NHR_4$, —$NR_4R_5$, —NH—C(O)—$R_4$, —$NR_4$—C(O)—$R_4$, —$CO_2R_4$, —$CO_2$—$NH_2$, —$CO_2$—$NHR_4$, —$CO_2$—$NR_4R_5$, wherein $R_4$ and $R_5$, independently of one another, signify $C_1$–$C_4$-alkyl, cyclohexyl, cyclohexylmethyl, phenyl or benzyl.

The heterocyclic radicals are bonded by a ring carbon atom to the oxygen atoms or the carbon atom of the carbonyl group in formula I.

Preferred substituents are methyl, ethyl, n- and i-propyl, n- and t-butyl, vinyl, allyl, methyloxy, ethyloxy, n- and i-propyloxy, n- and t-butyloxy, trifluoromethyl, trichloromethyl, β-hydroxyethyl, methoxy- or ethoxymethyl or -ethyl, trifluoromethoxy, cyclohexyl, cyclohexyloxy, cyclohexylmethyl, cyclohexylmethyloxy, phenyl, phenyloxy, benzyl, benzyloxy, phenylethyloxy, phenylethyl, halogen, —OH, —$OR_4$, —OC(O)$R_4$, —$NH_2$, —$NHR_4$, —$NR_4R_5$, —NH—C(O)—$R_4$, —$NR_4$—C(O)—$R_4$, —$CO_2R_4$, —$CO_2$—$NH_2$, —$CO_2$—$NHR_4$, —$CO_2$—$NR_4R_5$, wherein $R_4$ and $R_5$, independently of one another, signify $C_1$–$C_4$-alkyl, cyclohexyl, cyclohexylmethyl, phenyl or benzyl.

The aliphatic radical in question is preferably alkyl, which may be linear or branched, and preferably contains 1 to 8, most preferably 1 to 4 carbon atoms, or preferably alkenyl or alkynyl, which may be linear or branched and preferably contain 2 to 8, most preferably 2 to 4 carbon atoms. If $R_2$ and $R_3$ are alkenyl or alkynyl, the unsaturated bond is preferably in β-position to the oxygen atom. Examples are methyl, ethyl, n- and i-propyl, n-, i- and t-butyl, pentyl, i-pentyl, hexyl, heptyl, octyl, nonyl, decyl, undecyl and dodecyl, vinyl, allyl, ethynyl and propargyl. One preferred group of aliphatic radicals is methyl, ethyl, n- and i-propyl, n-, i- and t-butyl.

The cycloaliphatic radical in question is preferably cycloalkyl or cycloalkenyl with preferably 3 to 8, most preferably 5 or 6 ring carbon atoms. Some examples are cyclopropyl, cyclobutyl, cyclopentyl, cyclohexyl, cycloheptyl and cyclooctyl, as well as cyclopentenyl, cyclohexenyl and cyclohexadienyl. Cyclopentyl and cyclohexyl are preferred in particular.

The heterocycloaliphatic radical in question is preferably heterocycloalkyl or heterocyclo-alkenyl with preferably 3 to 6 carbon atoms, 4 to 7 ring members, and hetero atoms selected from the group —O— and —NR'—, wherein R' is H, $C_1$–$C_8$-alkyl, preferably $C_1$–$C_4$-alkyl, $C_5$- or $C_6$-cycloalkyl, $C_6$–$C_{10}$-aryl, for example phenyl or naphthyl, phenyl or phenylethyl. Some examples are pyrrolidinyl, pyrrolinyl, tetrahydrofuranyl, dihydrofuranyl and piperazinyl.

The cycloaliphatic-aliphatic radical in question is preferably cycloalkyt-alkyl or -alkenyl with preferably 3 to 8, most preferably 5 or 6 ring carbon atoms, and preferably 1 to 4, or 2–4, most preferably 1 or 2, or 2 or 3, carbon atoms in the alkyl group or alkenyl group. Some examples are cyclopentyl- or cyclohexylmethyl or -ethyl and cyclopentyl or cyclohexyl-ethenyl.

The heterocycloaliphatic-aliphatic radical in question is preferably heterocycloalkyl-alkyl or -alkenyl with preferably 3 to 6 carbon atoms, 4 to 7 ring members, and hetero atoms selected from the group —O— and —NR'—, wherein R' is H, $C_1$–$C_8$-alkyl, preferably $C_1$–$C_4$-alkyl, $C_5$- or $C_6$-cycloalkyl, $C_6$–$C_{10}$-aryl, for example phenyl or naphthyl, phenyl or phenylethyl, and preferably 1 to 4, most preferably 1 or 2, carbon atoms in the alkyl group, or 2 to 4 and most preferably 2 or 3 carbon atoms in the alkenyl group. Examples are pyrrolidinylmethyl or -ethyl or -ethenyl, pyrrolinylmethyl or -ethyl or -ethenyl, tetrahydrofuranylmethyl or -ethyl or -ethenyl, dihydrofuranylmethyl or -ethyl or -ethenyl, and piperazinylmethyl or -ethyl or -ethenyl.

The aromatic radicals in question are especially naphthyl and in particular phenyl.

The aromatic-aliphatic radicals in question are preferably phenyl- or naphthyl-$C_1$–$C_4$-alkyl or–$C_2$–$C_4$-alkenyl. Some examples are benzyl, naphthylmethyl, β-phenylethyl and β-phenyl-ethenyl.

The heteroaromatic radicals in question are preferably 5- or 6-membered, optionally condensed ring systems. Some examples are pyridinyl, pyrimidinyl, pyrazinyl, pyrrolyl, furanyl, oxazolyl, imidazolyl, benzofuranyl, indolyl, benzimidazolyl, quinolinyl, isoquinolinyl, quinazolinyl, quinoxalinyl.

The heteroaromatic-aliphatic radicals in question are preferably 5- or 6-membered, optionally condensed ring systems, which are bonded by one of their carbon atoms to the free bond of an alkyl group or alkenyl group, whereby the alkyl group contains preferably 1 to 4, most preferably 1 or 2 carbon atoms, and the alkenyl group contains preferably 2 to 4, most preferably 2 or 3 carbon atoms. Some examples are pyridinylmethyl or -ethyl or -ethenyl, pyrimidinylmethyl or -ethyl or -ethenyl, pyrrolylmethyl or -ethyl or -ethenyl, furanyl-methyl or -ethyl or -ethenyl, imidazolyl-methyl or -ethyl or -ethenyl, indolylmethyl or -ethyl or -ethenyl.

More preferred compounds of formula I include those wherein $R_1$, $R_2$ and $R_3$, independently of one another, signify linear or branched $C_1$–$C_8$-alkyl, $C_4$–$C_7$-cycloalkyl or $C_4$–$C_6$-hetreocycloalkyl with hetero atoms from the group O and N, $C_6$–$C_{10}$-aryl or $C_4$–$C_9$-heteroaryl with hetero atoms from the group O and N, $C_4$-$C_7$-cycloalkyl-$C_1$–$C_4$-alkyl or $C_3$–$C_6$-heterocycloalkyl-$C_1$–$C_4$-alkyl with hetero atoms from the group O and N, $C_6$–$C_{10}$-aryl-$C_1$–$C_4$-alkyl or $C_4$–$C_9$-heteroaryl-$C_1$–$C_4$-alkyl with hetero atoms from the group O and N, $R_1$ and $R_2$ together signify $C_1$–$C_4$-alkylene or $C_4$–$C_7$-1,2-cycloalkylene; or $C_2$–$C_4$-alkylene or $C_4$–$C_7$-cycloalkylene condensed with 1,2-phenylene, and $R_3$ has the above-mentioned significances, $R_2$ and $R_3$ together signify $C_1$–$C_4$-alkylene, $C_1$–$C_4$-alkylidene, $C_4$–$C_7$-1,2-cycloalkylene, $C_4$–$C_7$-cycloalkylidene, benzylidene, 1,2-phenylene, 1,2-pyridinylene, 1,2-naphthylene; or $C_3$–$C_4$-alkylene or $C_4$–$C_7$-cycloalkylene condensed with 1,2-cycloalkylene or with 1,2-phenylene, and $R_1$ has the above-mentioned significances, whereby $R_1$, $R_2$ and $R_3$ are unsubstituted or substituted by one or more, identical or different radicals selected from the group $C_1$–$C_4$-alkyl, $C_1$–$C_4$-alkoxy, $C_1$–$C_4$-halogenalkyl, $C_1$–$C_4$-hydroxyalkyl, $C_1$–$C_4$-alkoxymethyl or -ethyl, $C_1$–$C_4$-halogenalkoxy, cyclohexyl, cyclohexyloxy, cyclohexylmethyl, cyclohexylmethyloxy, phenyl, phenyloxy, benzyl, benzyloxy, phenylethyl, phenylethyloxy, halogen, —OH, —OR$_4$, —OC(O)R$_4$, —NH$_2$, —NHR$_4$, —NR$_4$R$_5$, —NH—C(O)—R$_4$, —NR$_4$—C(O)—R$_4$, —CO$_2$R$_4$, —CO$_2$—NH$_2$, —CO$_2$—NHR$_4$, —CO$_2$—NR$_4$R$_5$, wherein R$_4$ and R$_5$, independently of one another, signify C$_1$–C$_4$-alkyl, cyclohexyl, phenyl or benzyl.

One preferred sub group of the compounds of formula I is those wherein R$_1$, R$_2$ and R$_3$, independently of one another, signify linear or branched C$_1$–C$_4$-alkyl, C$_2$–C$_4$-alkenyl, C$_5$–C$_6$-cycloalkyl, phenyl, phenylethenyl, C$_5$–C$_6$-cycloalkyl-C$_1$–C$_2$-alkyl or C$_6$–C$_{10}$-aryl-C$_1$–C$_2$-alkyl, R$_1$ and R$_2$ together signify C$_1$–C$_3$-alkylene or C$_5$–C$_6$-1,2-cycloalkylene, R$_2$ and R$_3$ together signify C$_2$–C$_4$-alkylene, C$_1$–C$_4$-alkylidene, C$_5$–C$_6$-1,2-cycloalkylene, C$_5$–C$_6$-cycloalkylidene, benzylidene, 1,2-phenylene, whereby R$_1$, R$_2$ and R$_3$ are unsubstituted or substituted as above.

One especially preferred sub group of the compounds of formula I is those wherein R$_1$ signifies C$_1$–C$_4$-alkyl, C$_2$–C$_4$-alkenyl, cyclohexyl, phenyl, benzyl, phenylethyl or phenylethenyl, R$_2$ and R$_3$, independently of one another, signify linear or branched C$_1$–C$_4$-alkyl, cyclohexyl, phenyl, benzyl or phenylethyl, R$_1$ and R$_2$ together signify C$_2$–C$_3$alkylene or 1,2-cyclohexylene, R$_2$ and R$_3$ together signify C$_2$–C$_3$-alkylene, C$_1$–C$_4$-alkylidene, 1,2-cycohexylene, cyclohexylidene, benzylidene or 1,2-phenylene, whereby R$_1$, R$_2$ and R$_3$ are unsubstituted or substituted by methyl, ethyl, n- and i-propyl, n- and t-butyl, vinyl, allyl, methyloxy, ethyloxy, n- and i-propyloxy, n- and t-butyloxy, trifluoromethyl, trichloromethyl, β-hydroxyethyl, methoxy- or ethoxymethyl or -ethyl, trifluoro-methoxy, cyclohexyl, cyclohexyloxy, cyclohexylmethyl, cyclohexylmethyloxy, phenyl, phenyloxy, benzyl, benzyloxy, phenylethyloxy, phenylethyl, halogen, —OH, —OR$_4$, —OC(O)R$_4$, —NH$_2$, —NHR$_4$, —NR$_4$R$_5$, —NH—C(O)—R$_4$, —NR$_4$—C(O)—R$_4$, —CO$_2$R$_4$, —CO$_2$—NH$_2$, —CO$_2$—NHR$_4$, —CO$_2$—NR$_4$R$_5$, wherein R$_4$ and R$_5$, independently of one another, signify C$_1$–C$_4$-alkyl, cyclohexyl, cyclohexylmethyl, phenyl or benzyl.

α-ketoacetals are known or may be produced in a manner known per se by reacting alcohols with α-ketoaldehydes whilst removing the reaction water.

The ketoacetals, especially those of formula I, are hydrogenated to chiral secondary alcohols of formula II,

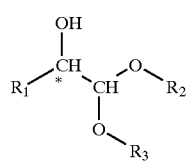

(II), wherein R$_1$, R$_2$ and R$_3$ have the significances given above and the symbol * primarily denotes the R- or S-form of one of the stereoisomers.

Platinum catalysts are known, have been described many times and are commercial. Platinum may be used both in metal form, for example as a powder, and, preferably, as platinum metal applied to finely-dispersed carriers. Suitable carriers are for example carbon, metal oxides, for example SiO$_2$, TiO$_2$, Al$_2$O$_3$, metal salts, and natural or synthetic silicates. The catalyst in question may also be a platinum colloid. The amount of platinum metal on the carrier may be for example 1 to 10, preferably 3 to 8% by weight, based on the carrier. Prior to usage, the catalysts may be activated by means of treatment with hydrogen at an elevated temperature or by ultrasound.

Chiral and aromatic nitrogen bases as modifiers for the platinum-catalysed enantoselective hydrogenation are similarly known, and are described for example by H.-U. Blaser et al. in Catalysis Today 37 (1997), pages 441 to 463. The nitrogen bases that are suitable are, in particular, those containing an aromatic or heteroaromatic, mononuclear or multinuclear ring, preferably mono- to trinuclear ring, optionally in combination with condensed cycloaliphatic or heterocycloaliphatic rings, whereby the basic N-atom(s) is or are bound in β- and preferably in α-position to a chiral carbon atom, and are ring members of a chiral N-cycloheteroaliphatic ring, or are bound to a ring by a chiral C$_1$- or C$_2$-group.

Preference is given to cinchona alkaloids and derivatives thereof. They may correspond, for example, to formula III

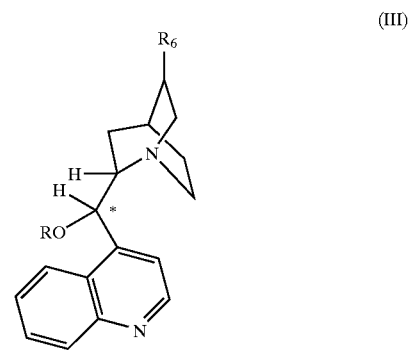

(III)

wherein R signifies H, C$_1$–C$_4$-alkyl, C$_1$–C$_4$-alkyl-C(O)C, C$_1$–C$_4$-hydroxyalkyl-C(O)O—, phenyl-C(O)O— or benzyl-C(O)O—, R$_6$ is H, C$_1$–C$_4$-alkyl, C$_1$–C$_4$-hydroxyalkyl, or C$_2$–C$_4$-alkenyl, and the symbol * denotes the R- or S-form of the stereo centres. Preferred cinchona alkaloids are those in which, in formula III, R$_6$ signifies H, methyl, ethyl or vinyl, and R is H, methyl, ethyl and acetyl.

The choice of nitrogen base determines which of the enantiomeric α-hydroxyacetals is primarily formed.

The catalyst metal may be used for example in an amount of 0.01 to 10, preferably 0.05 to 50, most preferably 0.1 to 10% by weight, based on the α-ketoacetal employed, whereby amounts of 0.1 to 5% by weight, or 0.1 to 1% by weight, are generally sufficient.

The nitrogen base is used for example in an amount of 0.1 to 1000, preferably 1 to 500, most preferably 10 to 200% by weight, based on the platinum metal employed. The nitrogen base may be added to the reaction vessel together with the platinum metal catalyst, or the platinum metal catalyst may already be impregnated with the nitrogen base, for example a cinchona alkaloid.

Hydrogenation Is preferably carried out at a hydrogen pressure of up to 200 bar, more preferably up to 150 bar, most preferably 10 to 100 bar.

The reaction temperature may be for example −50 to 100° C., more preferably 0 to 50° C., most preferably 0 to 35° C.

The reaction may be carried out without or in an inert solvent. Suitable solvents are for example aliphatic, cycloaliphatic and aromatic hydrocarbons (pentane, hexane, petroleum ether, cyclohexane, methylcyclohexane, benzene, toluene, xylene), ethers (diethyl ether, dibutyl ether, ethylene glycol dimethyl ether, ethylene glycol diethyl ether, diethylene glycol dimethyl ether, tetrahydrofuran, dioxane), alcohols (methanol, ethanol, propanol, butanol, ethylene glycol, diethylene glycol, ethylene glycol monomethyl or monoethyl ether, diethylene glycol monomethyl or monoethyl ether), ketones (acetone, methyl isobutyl ketone), carboxylates and lactones (ethyl or methyl acetate, valerolactone), N-substituted carboxylamides and lactams (dimethylformamide, N-methylpyrrolidone) and carboxylic acids (acetic acid, propionic acid, butyric acid). The optimum yield may be influenced by the choice of solvent. Carboxylic acids such as acetic acid have proved to be particularly suitable for this purpose.

The process according to the invention may be carried out, for example, whereby the catalyst with the nitrogen base is placed in an autoclave, optionally with a solvent, then the α-ketoacetal is added, afterwards the air is displaced with an inert gas, for example noble gases, hydrogen pressure is applied, and then the reaction is started, if required whilst stirring or agitating, and hydrogenation takes place until the up-take of hydrogen is no longer observed. The α-hydroxyacetal formed may be isolated and purified by conventional methods, for example distillation, crystallisation and chromatography.

The α-hydroxyacetals that can be produced according to the invention are valuable intermediates in the production of natural active ingredients [B. T. Cho et al. in Tetrahedron: Asymmetry Vol. 5, No. 7 (1994), pages 1147 to 1150], and synthetic pharmaceutical active ingredients and pesticides. The obtainable α-hydroxyacetals may be first converted into derivatives by known methods, and these may then be used as intermediates in the production of active ingredients. Acidic hydrolysis leads to 1,4-dioxanes or the corresponding aldehydes, which are either hydrogenated to 1,2-diols with a secondary optically active hydroxyl group, or reacted with amines in the presence of phenylboric acids to form optionally substituted optically active 1-phenyl-1-amino-2-hydroxyalkanes. After protection of the OH group, e.g. by means of a reaction with benzyl bromide, a reaction with strong acids will produce the hydroxyl-protected aldehydes, which may be hydrogenated to 1,2-diols, or may be converted by oxidation (for example with chromium trioxide) and removal of the protecting group to R- or S-α-hydroxycarboxylic acids.

The following examples illustrate the invention more fully. The optical yield is determined by gas chromatography using a Beta-dex column from the company Supelco (Article no. 2-4301), with hydrogen as the carrier gas and at elevated temperatures; or by HPLC (Chiracel OD column, with hexane and isopropanol 95:5). The reaction rate is determined by $^1$H-NMR.

EXAMPLES 1–6

Hydrogenation of 1,1-Dimethoxyacetone 5 mg of methoxyhydrocinchonidine (MeOHCd) or hydrocinchonidine (HCd) are placed in a 50 ml pressure autoclave having a magnetic stirrer and circuit breaker and then mixed with 50 mg of platinum on $Al_2O_3$ that has been made into a suspension with 10 ml of solvent (pre-treated for 2 hours at 400° C. under hydrogen). Then, 2 ml of 1,1-dimethoxyacetone in 10 ml of solvent are added and the autoclave is closed. It is rinsed three times with argon, three times with hydrogen and then 60 bars hydrogen pressure is applied. The reaction is started by switching on the stirrer. The temperature is kept constant at 25° C. by a cryostat. The pressure is kept constant by using a domed pressure regulator and the hydrogen up-take is measured by the reduction in pressure in a reservoir. When the reaction has ended, the pressure in the autoclave is released, then the autoclave is rinsed three times with argon and opened. The catalyst is filtered off and the reaction product is examined by gas chromatography at 60° C. The retention times are for 1,1-dimethoxyacetone 4.15 minutes, for (R)-1,1-dimethoxy-2-hydroxypropane 7.17 minutes and for (S)-1,1-dimethoxy-2-hydroxy-propane 7.95 minutes. The results are summarised in Table 1.

TABLE 1

| Ex. no. | solvent | cinchonidine | reaction time (minutes) | $H_2$ up-take | yield (g) | reaction rate (%) | optical yield (ee, %) |
|---|---|---|---|---|---|---|---|
| 1) | acetic acid | MeOHCd | 60 | 90% | 2.64[2] | 100 | 97 |
| 2 | acetic acid | MeOHCd | 51 | 91% | 2.48[2] | 100 | 96 |
| 3[5] | none | HCd | 93 | 84% | 11.89[3] | 88 | 80 |
| 4 | toluene | HCd | 140 | 60% | 1.93 | 66 | 79 |
| 5 | ethanol | HCd | 110 | 93% | 1.62[4] | 100 | 61 |
| 6 | ethanol | MeOHCd | 420 | 49% | 1.93 | 100 | 35 |

[1])120 bars hydrogen pressure
[2])still contains solvent
[3])loss during filtration
[4])loss during drying
[5])15 ml 1,1-dimethoxyacetone, 350 mg catalyst and 35 mg HCd.

EXAMPLES 7 to 11

Hydrogenation of 1,1-Diethoxyacetophenone

The procedure of examples 1-6 is followed, also with 2 ml of 1,1-diethoxyacetophenone. The examination under gas chromatography is effected at 140° C. The retention times are for 1,1-diethoxyacetophenone 10.63 minutes, for one enantiomer of 1,1, -dimethoxy-2-hydroxy-2-phenylethane 12.15 minutes and for the other enantiomer of 1,1,-dimethoxy-2-hydroxy-2-phenylethane 12.36 minutes. The results are summarised in Table 2.

TABLE 2

| Ex. no. | solvent | cinchonidine | reaction time (minutes) | H$_2$ uptake | yield (g) | reaction rate (%) | optical yield (ee, %) |
|---|---|---|---|---|---|---|---|
| 7 | toluene | HCd | 120 | 15% | 1.94 | 19 | 81 |
| 8[1)] | toluene | HCd | 60 | 33% | 1.79 | 31 | 78 |
| 9 | ethanol | HCd | 155 | 43% | 1.88 | 43 | 51 |
| 10 | acetic acid | HCd | 290 | 47% | 1.99[2)] | 31 | 48 |
| 11 | acetic acid | MeOHCd | 120 | 25% | 2.14[2)] | 22 | 15 |

[1)]10 mg HCd and 100 mg catalyst
[2)]still contains solvent

EXAMPLES 12 to 14

Hydrogenation of 2-Acetyl-1,3-dioxane

The procedure of examples 1–6 is followed with 1 ml of 2-acetyl-1,3-dioxane, 2.5 mg of nitrogen base, 25 mg of catalyst and 15 ml of solvent. The examination under gas chromatography is effected at 90° C. The retention times are for 2-acetyl-1,3-dioxane 7.85 minutes, for one enantiomer 9.5 minutes, and for the other enantiomer 9.83 minutes. The results are summarised in Table 3.

TABLE 3

| Ex. no. | solvent | cinchonidine | reaction time (minutes) | H$_2$ uptake | yield (g) | reaction rate (%) | optical yield (ee, %) |
|---|---|---|---|---|---|---|---|
| 12 | ethanol | MeOHCd | 180 | 39% | 0.78 | 46 | 64 |
| 13 | acetic acid | MeOHCd | 90 | 105% | 0.26[1)] | 100 | >97 |
| 14 | toluene | HCd | 220 | 26% | 0.90 | 27 | 75 |

[1)]loss during drying

EXAMPLES 15 to 17

Hydrogenation of 1,1-Diethoxyacetone

The procedure of examples 1–6 is followed with 1 ml of 1,1-diethoxyacetone, 2.5 mg of nitrogen base, 25 mg of catalyst and 15 ml of solvent. The examination under gas chromatography is effected at 60° C. The retention times are for 1,1-diethoxyacetone 9.32 minutes, for one enantiomer 13.22 minutes and for the other enantiomer 13.92 minutes. The results are summarised in Table 4.

TABLE 4

| Ex. no. | solvent | cinchonidine | reaction time (minutes) | H$_2$ uptake | yield (g) | reaction rate (%) | optical yield (ee, %) |
|---|---|---|---|---|---|---|---|
| 15 | ethanol | HCd | 160 | 51% | 0.62 | 50 | 41 |
| 16[1)] | acetic acid | MeOHCd | 65 | 89% | 0.99 | 95 | 91 |
| 17 | toluene | HCd | 1260 | 39% | 0.78 | 10 | 73 |

[1)]5 mg cinchonidine and 50 mg catalyst

EXAMPLES 18 to 27

Hydrogenation of Further Ketoacetals

The procedure of examples 1–6 is followed with 1 to 2 g of substrate, 5 to 50 mg of nitrogen base, 25 to 200 mg of catalyst 5% Pt on Al$_2$O$_3$ or SiO$_2$, and 15 to 25 ml of solvent. If not otherwise stated, the solvent used is ethyl acetate and the nitrogen base is MeOHCd.

Synthesis of educts. The educts of examples 18 and 19 are produced from methylglyoxal dimethylacetal by heating in ethanol or n-butanol with a strong acid as catalyst; that of example 20 is produced analogously from commercial 1,1-diethoxyacetophenone in methenol. The educts of examples 21 to 26 are produced analogously to T. Cuvigny et al., Synthesis, 1976, page 198. The educt of example 27 is produced as described by M. Tiecco et al. in J. Org. Chem., 55, 1990, page 4523. The reaction rate is determined by $^1$H-NMR. The results are given in Table 5.

TABLE 5

$$R-\underset{H}{\overset{O}{\underset{|}{C}}}-\underset{OR_1}{\overset{OR_1}{\underset{|}{C}}}-H \xrightarrow[\text{N-Base, }H_2]{Pt/Al_2O_3} R-\underset{H}{\overset{OH}{\underset{|}{C}}}-\underset{OR_1}{\overset{OR_1}{\underset{|}{C}}}-H$$

| Ex. no. | R | $R_1$ | reaction time (minutes) | $H_2$ uptake | reaction rate (%) | reaction speed (mmols/g · mln) | ee (%) |
|---|---|---|---|---|---|---|---|
| 18 | Me | Et | 140 | 92 | 86 | 5.8 | 91 |
| 19 | Me | n-Bu | 210 | 59 | 58 | 1.8 | 85 |
| 20[1)] | Ph | Me | 150 | 97 | 26 | 1.6 | 89 |
| 21 | $CH_3CH_2CH_2$ | Me | 120 | 96 | 96 | 4.0 | 93 |
| 22[1)] | $(CH_3)_2CHCH_2$ | Me | 900 | 30 | 9 | <0.1 | 62 |
| 23 | $PhCH_2CH_2$ | Me | 130 | 86 | >95 | 14.0 | 91 |
| 24 | $Ph-O-(CH_2)_3$ | Me | 75 | 104 | >95 | 4.2 | 93 |
| 25 | $CH_3CH_2-O-(CH_2)_3$ | Me | 65 | 111 | >95 | 5.3 | 92 |
| 26[1)] | $(CH_2)_2NOC-CH_2CH_2$ | Me | 235 | 71 | 55 | 0.7 | 80 |
| 27 | $CH_3OOC-CH_2CH_2$ | Me | 200 | — | 10 | <0.1 | 50 |

Me = methyl, Ph = phenyl, n-Bu = n-butyl, Et = ethyl
[1)]in toluene with HCd

The known compounds which are produced by the process according to the invention show good conformity with analytical results described in literature (NMR, GC, optical rotation). The products according to examples 22–27 are new. The results of characterisation are summarised in Table 6.

basic nitrogen atom adjacent to stereogenic carbon atoms, whereby prochiral α-ketoacetals are hydrogenated to optically active α-hydroxyacetals.

2. Process according to claim 1, whereby the prochiral α-ketoacetals are saturated or unsaturated, open-chained or

TABLE 6

| Example No. | $^1$H NMR (ppm relative to TMS in $CDCl_3$) | $^{13}$C NMR ($CDCl_3$) | mass spektroscopy | optical rotation |
|---|---|---|---|---|
| 22 | 4.10 (d, 1H), 3.65 (m, 1H), 3.50 (s, 3H), 3.45 (s, 3H), 2.1 (b, 1H), 1.9 (m, 1H), 1.45–1.30 (m, 2H), 0.95 (m, 6H) | 107.8, 69.8, 55.5, 55.3, 4.12, 24.6, 24.1, 21.9 | M-31: 131 (20) 75 (100) | $\alpha_D$ (c 2.05 in EtOH) = +40.9 |
| 23 | 7.3–7.15 (m, 5H), 4.15 (d, 1H), 3.65 (m, 1H), 3.50 (s, 3H), 3.40 (s, 3H), 2.90 (m, 1H), 2.75 (m, 1H), 2.20 (b, 1H), 1.95 (m, 1H), 1.80 (m, 1H) | 142.5, 128.9, 128.7, 1262, 107.3, 70.9, 55.5, 33.9, 32.1 | MH-31: 178 (10) 161 (10) 91 (40) 75 (100) | $\alpha_D$ (c 4.73 in EtOH) = +40.7 |
| 24 | 7.30 (m, 2H), 6.95 (m, 3H), 4.20 (d, 1H), 4.05 (m, 2H), 3.70 (m, 1H), 3.50 (s, 3H), 3.45 (s, 3H), 2.2 (b, 1H), 2.10–1.80 (m, 3H), 1.60 (m, 2H) | 159.4, 129.8, 121.0, 114.9, 107.4, 71.4, 68.2, 58.8, 55.6, 28.8, 25.8 | M + NH4 258 (100) 209 (100) 115 (25) | $\alpha_D$ (c 4.83 in EtOH) = +21.3 |
| 25 | 4.15 (d, 1H), 3.60 (m, 1H), 3.55–3.40 (m, 10H), 2.8 (b, 1H), 1.85–1.70 (m, 3H), 1.45 (m, 1H), 1.20 (t, 3H) | 107.7, 71.5, 71.1, 66.5, 55.5, 55.3, 29.5, 26.4, 15.5 | M-75: 117 (10) 115 (10) 75 (100) | $\alpha_D$ (c 4.88 in EtOH) = +29.7 |
| 26 | 4.20 (d, 1H), 3.65 (m, 1H), 3.45 (s, 6H), 3.30 (s, 1H), 3.05 (s 3H), 2.95 (s, 3H), 2.55 (m, 2H), 2.05 (m, 1H), 1.80 (m 1H) | 172.3, 105.8, 69.9, 54.0, 53.7, 36.1, 34.4, 28.6, 25.6 | M2Na: 433 (100) MH 206 (70) | $\alpha_D$ (c 5.06 in EtOH) = +21.3 |
| 27 | 4.15 (s, 1H), 3.70 (s, 3H), 3.65 (m, 1H), 3.50 (s, 3H), 3.45 (s, 3H), 2.60–2.40 (m, 2H), 2.25 (b, 1H), 1.95 (m, 1H), 1.75 (m, 1H) | 173.1, 105.5, 69.2, 53.9, 50.4, 28.9, 25.7 | M2Na: 407 (20) 256 (100) MNa 215 (70) | |

I claim:

1. Process for the heterogeneous and enantio-selective hydrogenation of prochiral organic α-keto compounds with platinum as the catalyst and in the presence of a soluble or immobilised chiral aromatic nitrogen base with at least one cyclic compounds, which are unsubstituted or substituted by radicals that are stable under the hydrogenation conditions.

3. Process according to claim 2, whereby the compounds contain 5 to 30 carbon atoms.

4. Process according to claim 1, whereby the α-ketoacetals correspond to formula I,

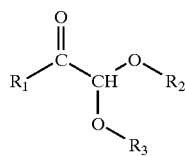

(I), wherein R₁, R₂ and R₃, independently of one another, signify a monovalent, saturated or unsaturated, aliphatic radical with 1 to 12 carbon atoms, a saturated or unsaturated cycloaliphatic radical with 3 to 8 carbon atoms, a saturated or unsaturated heterocycloaliphatic radical with 3 to 8 ring members and one or two hetero atoms from the group O, N and NR', a saturated or unsaturated cycloaliphatic-aliphatic radical with 4 to 12 carbon atoms, a saturated or unsaturated heterocycloaliphatic-aliphatic radical with 3 to 12 carbon atoms and one or two hetero atoms from the group O, N and NR', an aromatic radical with 6 to 10 carbon atoms, a heteroaromatic radical with 4 to 9 carbon atoms and one or two hetero atoms from the group O and N, an aromatic-aliphatic radical with 7 to 12 carbon atoms or a heteroaromatic-aliphatic radical with 5 to 11 carbon atoms and one or two hetero atoms from the group O and N, whereby R' is H, $C_1$–$C_8$-alkyl, $C_5$- or $C_6$-cyclo-alkyl, $C_6$–$C_{10}$-aryl, $R_1$ and $R_2$ together are $C_1$–$C_6$-alkylene or $C_3$–$C_8$-1,2-cycloalkylene; or $C_2$–$C_4$-alkylene or $C_3$–$C_8$-cycloalkylene which are condensed with 1,2-phenylene, $R_2$ and $R_3$ together signify $C_1$–$C_6$-alkylene, $C_1$–$C_8$-alkylidene, $C_3$–$C_8$-1,2-cycloalkylene, $C_3$–$C_8$-cycloalkylidene, benzylidene, 1,2-phenylene, 1,2-pyridynylene, 1,2-naphthylene; or C3–$C_4$-alkylene or $C_3$–$C_8$-1,2-cycloalkylene which are condensed with 1,2-cycloalkylene or with 1,2-phenylene, and R₁, R₂ and R₃ are unsubstituted or substituted by one or more identical or different radicals selected from the group $C_1$–$C_4$-alkyl, $C_2$–$C_4$-alkenyl, $C_1$–$C_4$-alkoxy, $C_1$–$C_4$-halogen-alkyl, $C_1$–$C_4$-hydroxyalkyl, $C_1$–$C_4$-alkoxymethyl or -ethyl, $C_1$–$C_4$-halogenalkoxy, cyclohexyl, cyclohexyloxy, cyclohexylmethyl, cyclohexylmethyloxy, phenyl, phenyloxy, benzyl, benzyloxy, phenylethyl, phenylethyloxy, halogen, —OH, —OR₄, —OC(O)—R₄, —NH₂, —NHR₄, —NR₄R₅, —NH—C(O)—R₄, —NR₄—C(O)—R₄, —CO₂R₄, —CO₂—NH₂, —CO₂—NHR₄, —CO₂—NR₄R₅, wherein R₄ and R₅, independently of one another, signify $C_1$–$C_4$-alkyl, cyclohexyl, cyclohexylmethyl, phenyl or benzyl.

5. Process according to claim 4, whereby the substituents are selected from the group methyl, ethyl, n- and 1-propyl, n- and t-butyl, vinyl, allyl, methyloxy, ethyloxy, n- and i-propyl-oxy, n- and t-butyloxy, trifluoromethyl, trichloromethyl, β-hydroxyethyl, methoxy- or ethoxymethyl or -ethyl, trifluoromethoxy, cyclohexyl, cyclohexyloxy, cyclohexylmethyl, cyclohexyl-methyloxy, phenyl, phenyloxy, benzyl, benzyloxy, phenylethyloxy, phenylethyl, halogen, —OH, —OR₄, —OC(O)R₄, —NH₂, —NHR₄, —NR₄R₅, —NH—C(O)—R₄, —NR₄—C(O)—R₄, —CO₂R₄, —CO₂—NH₂, —CO₂—NHR₄, —CO₂—NR₄R₅, wherein R₄ and R₅, independently of one another, signify $C_1$–$C_4$-alkyl, cyclohexyl, cyclohexylmethyl, phenyl or benzyl.

6. Process according to claim 1, whereby the catalyst employed is platinum in metal form, as a colloid or platinum metal applied to finely dispersed carriers.

7. Process according to claim 1, whereby the catalyst metal is used in an amount of 0.1 to 10% by weight, based on the α-ketoacetal employed.

8. Process according to claim 1, whereby the nitrogen base is a cinchona alkaloid of formula III

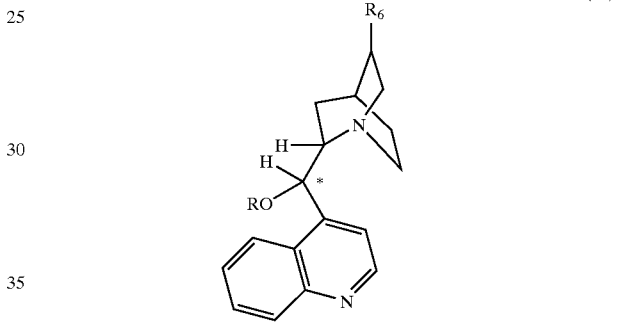

(III)

wherein R signifies H, $C_1$–$C_4$-alkyl, $C_1$–$C_4$-alkyl-C(O)C—, $C_1$–$C_4$-hydroxyalkyl-C(O)O—, phenyl-C(O)O— or benzyl-C(O)O—, R₆ is H, $C_1$–$C_4$-alkyl, $C_1$–$C_4$-hydroxyalkyl, or $C_2$–$C_4$-alkenyl, and the symbol * denotes the R- or S-form of the stereo centres.

9. Process according to claim 1, whereby the nitrogen base is used in an amount of 0.1 to 1000% by weight, based on the platinum metal employed.

10. Process according to claim 1, whereby the process is carried out at a pressure of up to 200 bar, and at a temperature of 0 to 100° C.

11. The process according to claim 4, wherein R' is $C_1$–$C_4$-alkyl, phenyl, naphthyl or phenylethyl.

* * * * *